(12) United States Patent
Sheiner et al.

(10) Patent No.: US 11,806,094 B2
(45) Date of Patent: Nov. 7, 2023

(54) CATHETER MOTION TRACE VISUALIZATION

(71) Applicant: BIOSENSE WEBSTER (ISRAEL) LTD., Yokneam (IL)

(72) Inventors: Amiram Sheiner, Zichron yaakov (IL); Assaf Cohen, Kiryat Bialik (IL); Ilya Shtirberg, Nesher (IL); Maxim Galkin, Haifa (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 553 days.

(21) Appl. No.: 16/809,654

(22) Filed: Mar. 5, 2020

(65) Prior Publication Data

US 2020/0315714 A1    Oct. 8, 2020

Related U.S. Application Data

(60) Provisional application No. 62/828,925, filed on Apr. 3, 2019.

(51) Int. Cl.
*A61B 34/20* (2016.01)
*A61B 34/00* (2016.01)
(Continued)

(52) U.S. Cl.
CPC .......... *A61B 34/25* (2016.02); *A61B 18/1492* (2013.01); *A61B 34/20* (2016.02);
(Continued)

(58) Field of Classification Search
CPC ..... A61B 34/25; A61B 18/1492; A61B 34/20; A61B 90/37; A61B 2018/00357; A61B 2018/00577; A61B 2034/105; A61B 2034/252; A61B 2090/367; A61B 2018/00702; A61B 2018/00839;
(Continued)

(56) References Cited

U.S. PATENT DOCUMENTS 7,263,397 B2    8/2007   Hauck
8,571,351 B2 *   10/2013   Yang .................... G06V 10/757
                                                       382/294
(Continued)

OTHER PUBLICATIONS

European Search Report for corresponding EPA No. 20167699.6 dated Jul. 30, 2020.

*Primary Examiner* — Saptarshi Mazumder

(57) ABSTRACT

Methods, apparatus and computer software products implement embodiments of the present invention that include applying energy to a probe that is in contact with tissue in a body cavity so as to ablate the tissue. While applying the energy, signals are received from a location transducer in the probe, which are indicative of a location of the probe in the cavity. The signals are processed so as to derive 3D location coordinate points corresponding to the location of the probe at a sequence of times during which the energy was applied. While applying the energy, a 3D representation of the body cavity is rendered to a display, and visual indicators are superimposed on the 3D representation, the visual indicators corresponding to the 3D location coordinate points at the sequence of times. Finally, a linear trace connecting the coordinate points in accordance with the sequence is superimposed on the 3D representation.

15 Claims, 3 Drawing Sheets

(51) Int. Cl.
*A61B 90/00* (2016.01)
*A61B 18/14* (2006.01)
*A61M 25/01* (2006.01)
*A61B 34/10* (2016.01)
*A61B 18/00* (2006.01)

(52) U.S. Cl.
CPC ......... *A61B 90/37* (2016.02); *A61M 25/0105* (2013.01); *A61B 2018/00357* (2013.01); *A61B 2018/00577* (2013.01); *A61B 2034/105* (2016.02); *A61B 2034/252* (2016.02); *A61B 2090/367* (2016.02); *A61M 25/0127* (2013.01); *A61M 2025/0166* (2013.01)

(58) Field of Classification Search
CPC .... A61B 2018/00875; A61M 25/0105; A61M 25/0127; A61M 2025/0166
See application file for complete search history.

(56) References Cited

U.S. PATENT DOCUMENTS

| | | |
|---|---|---|
| 2008/0255505 A1 | 10/2008 | Carlson |
| 2009/0027398 A1* | 1/2009 | Frisken .................. G06T 11/203 345/442 |
| 2010/0256558 A1 | 10/2010 | Olson |
| 2011/0046773 A1* | 2/2011 | Iwashita ............ G05B 19/4097 700/182 |
| 2012/0209260 A1 | 8/2012 | Lambert |
| 2013/0281839 A1 | 10/2013 | Yan |
| 2014/0364848 A1* | 12/2014 | Heimbecher ...... A61B 18/1206 606/41 |
| 2017/0120080 A1 | 5/2017 | Phillips |
| 2017/0128128 A1 | 5/2017 | Saba |
| 2018/0070855 A1* | 3/2018 | Eichler .................. A61B 5/743 |
| 2018/0360342 A1 | 12/2018 | Fuimaono |

* cited by examiner

CATHETER MOTION TRACE VISUALIZATION

CROSS-REFERENCE TO RELATED APPLICATIONS

This application claims the benefit of U.S. Provisional Patent Application 62/828,925, filed Apr. 3, 2019, which is incorporated herein by reference.

FIELD OF THE INVENTION

The present invention relates generally to medical imaging, and specifically to generating and presenting a three-dimensional representation of a body cavity that traces locations of a treatment catheter during an ablation procedure.

BACKGROUND OF THE INVENTION

Some medical procedures, such as ablating tissue in a body organ (e.g., a heart), are performed by inserting a medical probe into the organ. The medical probe comprises an ablation electrode that can deliver radio frequency (RF) energy to ablate tissue in contact with the electrode in order to provide a therapeutic result. In alternative configurations, the medical probe can deliver a different energy source such as laser, ultrasound, or cryogenic cooling in order to provide the therapeutic result.

U.S. Patent Application 2012/0209260 to Lambert et al. describes a method for predicting atrial wall electrical reconnection based on contact force measured during RF ablation. The method includes presenting a trace line showing the order in which lesions are formed during an ablation.

U.S. Patent Application 2013/0281839 to Yan et al. describes a method for visualizing a catheter during a three-dimensional ultrasound procedure. The method includes using an illustrated geometric constraint that reduces a six degree of freedom ("DOF") catheter tracking problem [x, y, z, a, b, c], where xyz are translations and a, b, and c are rotations, into a four DOF problem with [r, a, b, c], where r is a translation along a tracing line associated with the catheter tip.

U.S. Patent Application 2010/0256558 to Olson et al. describes a robotic system for manipulating a catheter. The system includes a user interface that enables a user to select target points that may be used to identify lesion points for intended or completed therapy delivery, way-points for semi-automated step-wise catheter movement, destination points for fully automated movement, or as relative markers or virtual electrophysiology sensors that may have no impact on relative movement.

U.S. Patent Application 2008/0255505 to Carlson et al. describes a user interface for controlling a robotic catheter system. The user interface presents, to an operator, a catheter within or relative to a three dimensional (3D) space, such as a body cavity or organ, e.g., a chamber of a patient's heart. The operator can use a mouse to click points in the body cavity, and the user interface projects, into the 3D space, a trace line that can be used to guide the robotic catheter.

SUMMARY OF THE INVENTION

There is provided, in accordance with an embodiment of the present invention, a method for monitoring a medical procedure, including applying energy to a probe that is in contact with tissue in a cavity within a body of a living subject so as to ablate the tissue, while applying the energy, receiving, by a processor, signals from a location transducer in the probe, which are indicative of a location of the probe in the cavity, processing the signals so as to derive three-dimensional (3D) location coordinate points corresponding to the location of the probe at a sequence of times during which the energy was applied, and while applying the energy, rendering to a display a 3D representation of the body cavity, and superimposing on the 3D representation visual indicators corresponding to the 3D location coordinate points at the sequence of times together with a linear trace connecting the coordinate points in accordance with the sequence.

In one embodiment, the cavity includes a chamber of a heart.

The some embodiments, the method also includes rendering a bounding sphere having a surface that encloses the visual indicators.

In a first embodiment, the bounding sphere includes a minimal bounding sphere.

In a second embodiment, the method further includes computing a weighted average of the 3D location coordinate points, and rendering the bounding sphere includes centering the bounding sphere at a graph location in the 3D representation corresponding to the weighted average of the 3D location coordinate points.

In a third embodiment, the method additionally includes counting, during the sequence of times, respective numbers of instances of each of the 3D location coordinate points, and rendering the bounding sphere includes centering the bounding sphere at a graph location in the 3D representation corresponding to 3D location point having a highest number of the instances.

In another embodiment, the visual indicators and visual trace include a continuous line that traverses graph locations on the 3D representation corresponding to the sequence of coordinate points.

In an additional embodiment, the visual trace includes line segments connecting each sequential pair of the visual indicators.

In a further embodiment, the method also includes counting, during the sequence of times, respective numbers of instances of each of the 3D location coordinate points, and superimposing each given visual indicator includes rendering a given visual indicator using a color based on the respective number of instances of the given visual indicator.

In a supplemental embodiment, the method additionally includes specifying a threshold number, and wherein upon detecting that a number of the 3D location coordinate points exceeds the threshold number, superimposing the visual indicators includes rendering, to the display, the visual indicators corresponding to the threshold number of the most recent 3D coordinate points.

In another embodiment, the method further includes specifying a threshold time period, and wherein upon the sequence of times exceeding the threshold time period, superimposing the visual indicators includes rendering, to the display, the visual indicators corresponding to the 3D coordinate points during the most recent threshold time period.

There is also provided, in accordance with an embodiment of the present invention, a medical apparatus for monitoring a medical procedure, including a probe, an ablation module configured to apply energy to the probe that is in contact with tissue in a cavity within a body of a living subject so as to ablate the tissue, a display, and a processor configured to receive, while the ablation module applies the energy, signals from a location transducer in the probe, which are indicative of a location of the probe in the cavity, to process the signals so as to derive three-dimensional (3D) location coordinate points corresponding to the location of the probe at a sequence of times during which the energy was applied, and while the ablation module applies the energy, to render to the display a 3D representation of the body cavity, and to superimpose on the 3D representation visual indicators corresponding to the 3D location coordinate points at the sequence of times together with a linear trace connecting the coordinate points in accordance with the sequence.

There is additionally provided, in accordance with an embodiment of the present invention, a computer software product, operated in conjunction with an ablation module configured to apply energy to a probe that is in contact with tissue in a cavity within a body of a living subject so as to ablate the tissue, the product including a non-transitory computer-readable medium, in which program instructions are stored, which instructions, when read by a computer, cause the computer to receive, while the ablation module applies the energy, signals from a location transducer in the probe, which are indicative of a location of the probe in the cavity, to process the signals so as to derive three-dimensional (3D) location coordinate points corresponding to the location of the probe at a sequence of times during which the energy was applied, and while the ablation module applies the energy, to render to a display a 3D representation of the body cavity, and to superimpose on the 3D representation visual indicators corresponding to the 3D location coordinate points at the sequence of times together with a linear trace connecting the coordinate points in accordance with the sequence.

There is further provided, in accordance with an embodiment of the present invention, a method for monitoring a medical procedure, including receiving, by a processor, signals from a location transducer in a probe that is in contact with tissue in a cavity within a body of a living subject, the signals indicative of a location of the probe in the cavity, processing the signals so as to derive three-dimensional (3D) location coordinate points corresponding to the location of the probe at a sequence of times, and while the probe is in contact with the tissue, rendering to a display a 3D representation of the body cavity, superimposing on the 3D representation visual indicators corresponding to the 3D location coordinate points at the sequence of times together with a linear trace connecting the coordinate points in accordance with the sequence, and rendering to the display a bounding sphere having a surface that encloses the plurality of visual indicators.

In some embodiments, the bounding sphere includes a minimal bounding sphere.

In one embodiment, the method also includes computing a weighted average of the 3D location coordinate points, and rendering the bounding sphere includes centering the bounding sphere at a graph location in the 3D representation corresponding to the weighted average of the 3D location coordinate points.

In another embodiment, the method additionally includes counting, during the sequence of times, respective numbers of instances of each of the 3D location coordinate points, and rendering the bounding sphere includes centering the bounding sphere at a graph location in the 3D representation corresponding to a 3D location point having a highest number of instances.

There is also provided, in accordance with an embodiment of the present invention, a medical apparatus for monitoring a medical procedure, including a probe, a display, and a processor configured to receive signals from a location transducer in a probe that is in contact with tissue in a cavity within a body of a living subject, the signals indicative of a location of the probe in the cavity, to process the signals so as to derive three-dimensional (3D) location coordinate points corresponding to the location of the probe at a sequence of times, and while the probe is in contact with the tissue, to render to the display a 3D representation of the body cavity, to superimpose on the 3D representation visual indicators corresponding to the 3D location coordinate points at the sequence of times together with a linear trace connecting the coordinate points in accordance with the sequence, and to render to the display a bounding sphere having a surface that encloses the plurality of visual indicators.

There is additionally provided, in accordance with an embodiment of the present invention, a computer software product, operated in conjunction with a probe that is in contact with tissue in a cavity within a body of a living subject, the product including a non-transitory computer-readable medium, in which program instructions are stored, which instructions, when read by a computer, cause the computer to receive signals from a location transducer in the probe the signals indicative of a location of the probe in the cavity, to process the signals so as to derive three-dimensional (3D) location coordinate points corresponding to the location of the probe at a sequence of times, and while the probe is in contact with the tissue, to render to a display a 3D representation of the body cavity, to superimpose on the 3D representation visual indicators corresponding to the 3D location coordinate points at the sequence of times together with a linear trace connecting the coordinate points in accordance with the sequence, and to render to the display a bounding sphere having a surface that encloses the plurality of visual indicators.

BRIEF DESCRIPTION OF THE DRAWINGS

The disclosure is herein described, by way of example only, with reference to the accompanying drawings, wherein.

DETAILED DESCRIPTION OF EMBODIMENTS

When using a medical probe comprising a treatment electrode to treat tissue in a body cavity, it may be difficult to maintain stability of the treatment electrode. For example, when using an ablation catheter to ablate a specific region of intracardiac tissue during a cardiac ablation procedure, movement of the heart can make it difficult to keep the ablation catheter stable while the heart is moving (e.g., motion due to the cardiac cycle). This can be especially true during high power ablations having short durations. Additionally or alternatively, insufficient force applied by a distal end of the ablation catheter on the intracardiac tissue may result in the distal end slipping during the procedure.

Exemplary embodiments of the present invention provide a system and methods for monitoring a medical procedure (e.g., cardiac ablation) by tracing the motion of a medical probe (e.g., an ablation catheter) during the procedure. As described hereinbelow, energy is applied to a probe that is in contact with tissue in a cavity within a body of a living subject so as to ablate the tissue, and while the energy is applied, a processor receives signals from a location transducer in the probe, which are indicative of a location of the probe in the cavity. The signals are processed so as to derive three-dimensional (3D) location coordinate points corresponding to the location of the probe at a sequence of times during which the energy was applied. Finally, while applying the energy, a 3D representation of the body cavity is rendered to a display and visual indicators are superimposed on the 3D representation corresponding to the 3D location coordinate points at the sequence of times together with a linear trace connecting the coordinate points in accordance with the sequence.

By providing the linear trace during the procedure, systems implementing exemplary embodiments of the present invention can provide valuable real-time feedback to medical professionals regarding the effectiveness of the performed medical procedure, since the length of the linear trace is directly proportional to the amount of movement of the probe during the procedure.

System Description

Figure 1:
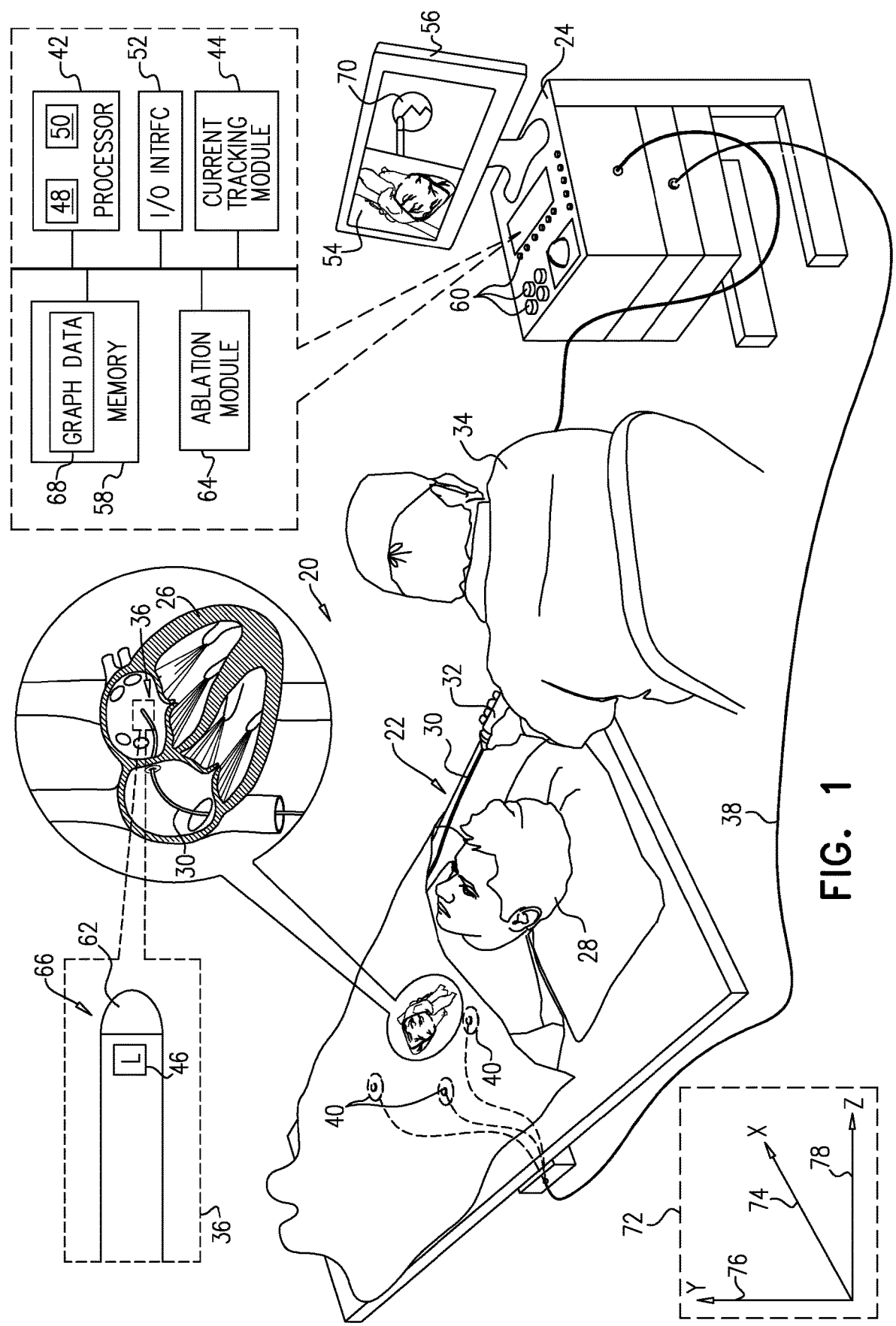
FIG. 1 is a schematic, pictorial illustration of a medical system comprising a control console and a medical probe having a treatment electrode affixed to its distal end, in accordance with an exemplary embodiment of the present invention.

FIG. 1 is a schematic, pictorial illustration of a medical system 20 comprising medical probe 22 and a control console 24, in accordance with an exemplary embodiment of the present invention. Medical system 20 may be based, for example, on the CARTO® system, produced by Biosense Webster Inc. of 33 Technology Drive, Irvine, Calif. 92618 USA. In exemplary embodiments described hereinbelow, medical probe 22 comprises an intracardiac catheter that can be used for diagnostic or therapeutic treatment, such as for ablating tissue in a heart 26 of a patient 28. Alternatively, medical probe 22 may be used, mutatis mutandis, for other therapeutic and/or diagnostic purposes in the heart or in other body organs.

Probe 22 comprises an insertion tube 30 and a handle 32 coupled to a proximal end of the insertion tube. By manipulating handle 32, a medical professional 34 can insert probe 22 into a body cavity in patient 28. For example, medical professional 34 can insert probe 22 through the vascular system of patient 28 so that a distal end 36 of probe 22 enters a chamber of heart 26 and engages intracardiac tissue at a desired location or locations.

Control console 24 is connected, by a cable 38, to body surface electrodes, which typically comprise adhesive skin patches 40 that are affixed to patient 28. In the configuration shown in FIG. 1, system 20 uses impedance-based position sensing to determine a location of distal end 36.

To implement impedance-based position sensing, control console 24 comprises a processor 42 that, in conjunction with a current tracking module 44, determines location coordinates of distal end 36 inside heart 26 based on impedances and/or currents measured between adhesive skin patches 40 and a location electrode 46 comprising an electrode that is affixed to distal end 36.

As stated above, in conjunction with current tracking module 44, processor 42 may determine location coordinates of distal end 36 inside heart 26 based on impedances and/or currents measured between adhesive skin patches 40 and location electrode 46. Such a determination is typically after a calibration process relating the impedances or currents to known locations of the distal end has been performed.

Processor 42 may comprise real-time noise reduction circuitry 48 typically configured as a field programmable gate array (FPGA), followed by an analog-to-digital (A/D) signal conversion integrated circuit 50. The processor can be programmed to perform one or more algorithms disclosed herein, each of the one or more algorithms comprising steps described hereinbelow. The processor uses circuitry 48 and circuit 50 as well as features of modules in FIG. 1 which are described herein, in order to perform the one or more algorithms.

The medical system shown in FIG. 1 uses impedance-based location transducer comprising adhesive skin patches 40 and electrode 46 to measure a location of distal end 36, but other position tracking techniques may be used (e.g., techniques using magnetic-based sensors). Impedance-based position tracking techniques are described, for example, in U.S. Pat. Nos. 5,983,126, 6,456,864 and 5,944,022, whose disclosures are incorporated herein by reference. Magnetic position tracking techniques that use a location transducer comprising a magnetic field sensor are described, for example, in U.S. Pat. Nos. 5,391,199, 5,443,489, 6,788,967, 6,690,963, 5,558,091, 6,172,499 and 6,177,792, whose disclosures are incorporated herein by reference. The methods of position sensing described hereinabove are implemented in the above-mentioned CARTO® system and are described in detail in the patents cited above.

Control console 24 also comprises an input/output (I/O) communications interface 52 that enables the control console to transfer signals from, and/or transfer signals to location electrode 46 and adhesive skin patches 40. Based on signals received from location electrode 46 and adhesive skin patches 40, processor 42 can generate a map 54 that shows the location of distal end 36 in the patient's body. During the procedure, processor 42 can present map 54 to medical professional 34 on a display 56, and store data representing the map in a memory 58. Memory 58 may comprise any suitable volatile and/or non-volatile memory, such as random access memory, a solid-state disk, or a hard disk drive.

In some exemplary embodiments, medical professional 34 can manipulate map 54 using one or more input devices 60. In alternative exemplary embodiments, display 56 may comprise a touchscreen that can be configured to accept inputs from medical professional 34, in addition to presenting map 54.

In the configuration shown in FIG. 1, probe 22 comprises a treatment electrode 62 that may comprise an ablation electrode, and control console 24 comprises an ablation module 64. In some exemplary embodiments, treatment electrode 62 is affixed to a distal tip 66 of probe 22, and may comprise gold overlaying the distal tip. Ablation module 64 can also be configured to monitor and control ablation parameters such as the level and the duration of ablation power (e.g., radio-frequency energy) conveyed to treatment electrode 62. In some exemplary embodiments, treatment electrode 62 can be configured to apply a signal to tissue in heart 26, and/or to measure a certain physiological property (e.g., the local surface electrical potential) at a location in the heart.

While the configuration in FIG. 1 shows probe 22 comprising location electrode 46 and treatment electrode 62, configurations where a single electrode (e.g., electrode 62) is used for both location sensing and ablation are considered to be within the spirit and scope of the present invention.

While medical professional 34 uses probe 22 to perform a medical procedure within a body cavity (e.g., heart 26) of patient 28, processor 42 can store locations of treatment electrode 62 to graph data 68 in memory 58. In exemplary embodiments of the present invention, processor 42 uses graph data 68 to generate a 3D representation 70, and present the 3D representation on display 56 during the medical procedure, as described in the description referencing FIGS. 2 and 4 hereinbelow.

As described supra, FIG. 1 uses impedance-based position sensing to determine a location and an orientation of distal end 36. In some exemplary embodiments the location and the orientation may comprise position coordinates in a three-dimensional coordinate system 72 comprising an X-axis 74, a Y-axis 76 and a Z-axis 78.

Location Tracking and Trace Visualization

Figure 2:
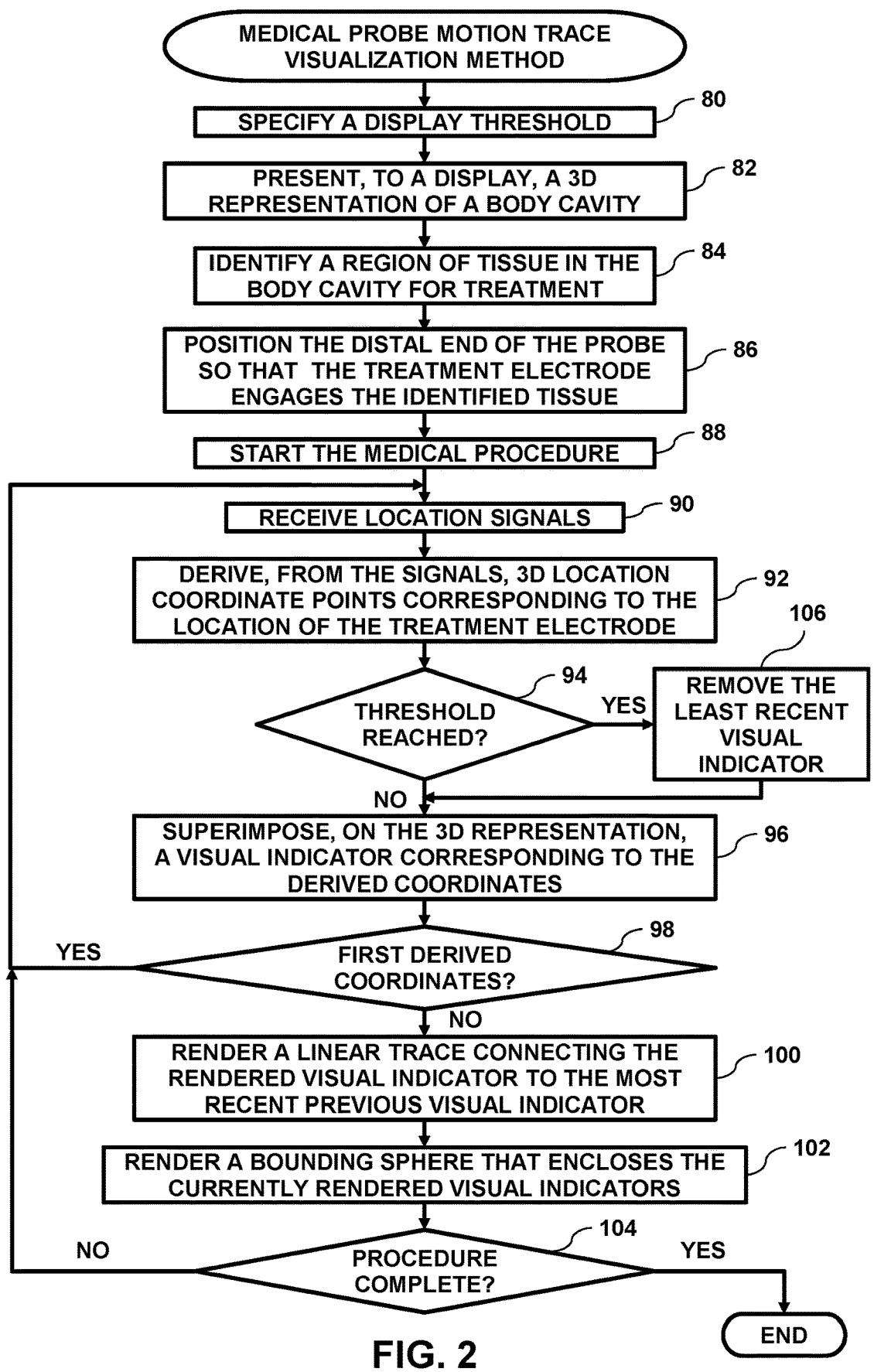
FIG. 2 is a flow diagram that schematically illustrates a method for presenting a three-dimensional (3D) representation that traces motion of the treatment electrode during a medical procedure, in accordance with an exemplary embodiment of the present invention.
Figure 3:
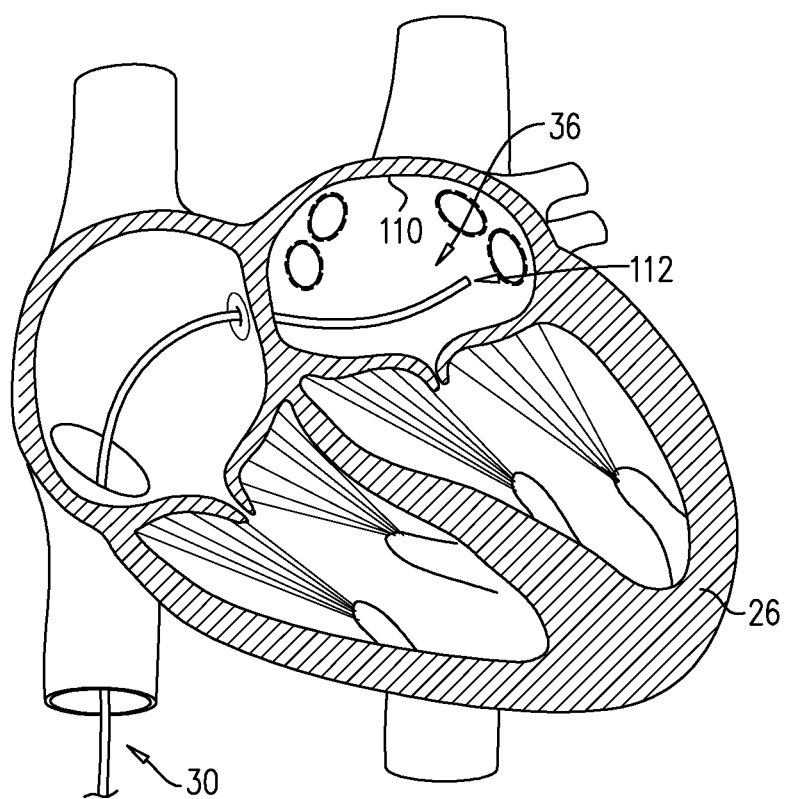
FIG. 3 is a schematic pictorial illustration of the distal end of the medical probe inside a cardiac chamber, in accordance with an exemplary embodiment of the present invention.

FIG. 2 is a flow diagram of an algorithm that schematically illustrates a method for generating and presenting the 3D representation 70 that traces motion of treatment electrode 62 during a medical procedure, and FIG. 3 is a schematic pictorial illustration of distal end 36 inside a chamber of heart 26 during the medical procedure, in accordance with an exemplary embodiment of the present invention.

Figure 4A:
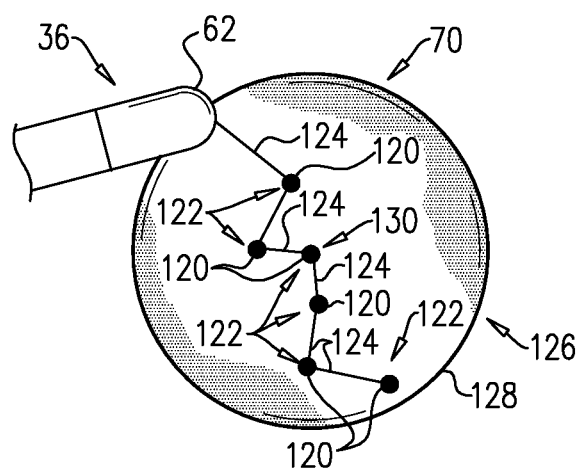
FIGS. 4A and 4B are schematic pictorial illustrations of the 3D representation, in accordance with exemplary embodiments of the present invention.
Figure 4B:
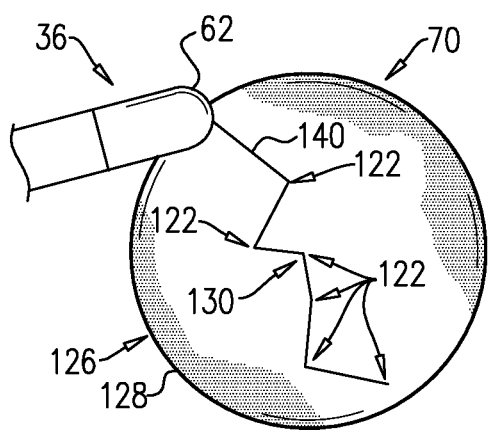

FIGS. 4A and 4B, referred to collectively as FIG. 4, are schematic pictorial illustrations of 3D representation 70, in accordance with exemplary embodiments of the present invention. In some exemplary embodiments, as shown in FIG. 4A, 3D representation 70 comprises a plurality of visual indicators 120 that correspond to respective probe locations 112 of treatment electrode 62 during a medical procedure.

In a specification step 80, processor 42 selects a display threshold. As described hereinbelow, processor 42 renders, to display 56, 3D representation 70 that presents locations of treatment electrode 62 during a medical procedure. To select the display threshold, processor 42 can retrieve the display threshold from memory 58, or receive a signal from one or more input devices 60 that indicates the display threshold.

In one exemplary embodiment, the display threshold may comprise a specific number of locations (e.g., 8, 10 or 12). In this exemplary embodiment, processor 42 can present 3D representation 70 comprising the specific number of the most recent locations of treatment electrode 62 during a medical procedure. In another exemplary embodiment, the display threshold may comprise a specified time period (e.g., 4, 6 or 8 seconds). In this exemplary embodiment, processor 42 can present 3D representation 70 presenting the locations of treatment electrode 62 during a medical procedure during the most recent specified time period.

In a first rendering step 82 processor 42 renders 3D representation 70 to display 56, and in an identification step 84, medical professional 34 identifies, on the map a region of intracardiac tissue 110 (FIG. 3) for treatment. In some exemplary embodiments, 3D representation 70 comprises a 3D representation of a given body cavity (e.g., heart 26) in patient 28, and may be based on a previously acquired 3D image of the given body cavity.

In a positioning step 86, medical professional 34 manipulates handle 32 in order to position distal end 36 so that treatment electrode 62 engages (i.e., is in contact with) the identified region of intracardiac tissue 110, and in a treatment step 88, medical professional 34 starts a medical procedure. As described supra, examples of medical procedures that can be performed using exemplary embodiments of the present invention include, but are not limited to, delivering ablation energy to intracardiac tissue 110, or measuring a certain physiological property (e.g., the local surface electrical potential) in the intracardiac tissue. To deliver ablation energy to intracardiac tissue 110, ablation module 64 applies energy to treatment electrode 62 that is in contact with the intracardiac tissue.

While the steps in the flow diagram describe treating intracardiac tissue 110 in heart 26, treating any tissue in any body cavity in patient 28 is considered to be within the spirit and scope of the present invention.

In a receive step 90, processor 42 receives, from adhesive skin patches 40, location signals indicating a given probe location 112 of electrode 46 in heart 26, and in step 92 the processor processes the received signals so as to derive, for treatment electrode 62, 3D location coordinate points (i.e., in 3D coordinate system 72) corresponding to the indicated location.

In a first comparison step 94, if the display threshold has not been reached, then in a superimposition step 96, processor 42 superimposes, on 3D representation 70, a visual indicator 120 corresponding to the probe location of treatment electrode in the given body cavity. As described supra, the display threshold may comprise a specific number of locations or a specific time period.

In a second decision step 98 if the 3D location coordinates derived in step 92 were the first 3D location coordinates derived during the medical procedure (i.e., that started in in step 90), then the method continues with step 90. However, if the derived 3D location coordinates are not the first derived location coordinates, then in a second rendering step 100, processor 42 renders, to display 56, a linear trace that connects the superimposed visual indicator 120 with the most recent previous visual indicator that processor 42 superimposed on 3D representation 70.

In the example presented in FIG. 4A, the linear trace comprises a sequence of line segments 124 that connect sequential pairs of visual indicators 120 at respective 3D representation locations 122 on 3D representation 70 that correspond to probe locations 112 of treatment electrode 62 during the procedure. For example, if 3D representation 70 comprises a sequence of first, second, third and fourth visual indicators 120, the sequential pairs of the visual indicators comprise the first and the second visual indicators, the second and the third visual indicators, and the third and the fourth visual indicators.

In the example shown in FIG. 4B, the linear trace comprises a single continuous line 140 that traverses graph locations 122 of 3D representation 70 that correspond to probe locations 112 of treatment electrode 62 during the procedure.

In a third rendering step 102, processor 42 renders, to display 56, a bounding sphere 126 comprising a surface 128 that encloses the currently rendered visual indicators 120. In one exemplary embodiment, bounding sphere 126 may comprise a minimal bounding sphere that can be defined as the bounding sphere with minimal radius among all possible bounding spheres 126.

In one exemplary embodiment, processor 42 can compute a center 130 of sphere 126 as a given graph location 122 on 3D representation 70 that corresponds to the most visited probe location 112 of treatment electrode 62 during the procedure. In some exemplary embodiments, processor can identify the most visited probe location 112 of treatment electrode 62 during the procedure by counting, during the medial procedure, respective numbers of instances of each of the 3D location coordinate points, and identifying a given probe location 112 having the highest number of instances.

In another exemplary embodiment, processor 42 can compute center 130 of sphere 126 as a given graph location 122 on 3D representation 70 that corresponds to a given location by computing a weighted average (i.e., based on location and time) of probe locations 112 of treatment electrode 62 during the procedure, and centering the sphere at the graph location corresponding to the computed weighted average In additional exemplary embodiments, processor 42 can compute, during the medical procedure, respective numbers of instances of each of the probe locations, and present each given visual indicator 120 in a color that corresponds to the amount of time the treatment electrode was positioned at the probe location corresponding to the given visual indicator. For example:

Processor 42 can present the given indicator 120 in yellow if the treatment was electrode was positioned at the given location for less than one second.

Processor 42 can present the given indicator 120 in green if the treatment was electrode was positioned at the given location between one and two seconds.

Processor 42 can present the given indicator 120 in red if the treatment was electrode was positioned at the given location for more than two seconds.

In a third comparison step 104, if medical professional 34 has completed the medical procedure (i.e., using treatment electrode 62), then the method ends. However, if the medical procedure is not completed, then the method continues with step 90.

Returning to step 94, if the display threshold has been reached, then in a removal step 106, processor 42, removes the least recent visual indicator from 3D representation 70 on display 56, and the method continues with step 96.

In a first example, if the display threshold comprises eight locations, upon processor 42 deriving the ninth 3D location coordinate points during the procedure, the processor detects that the display threshold has been reached, and removes, from 3D representation 70, the visual indicator corresponding to the first location coordinate points derived during the procedure, and adds, to the 3D representation, a new visual indicator 120 corresponding to the ninth location coordinate points derived during the procedure.

In a second example, if the display threshold comprises ten seconds, upon processor 42 deriving location coordinate points during the eleventh second of the procedure, the processor detects that the display threshold has been reached, and removes, from 3D representation 70, the visual indicator corresponding to the location coordinate points derived during the first second of the procedure, and adds, to the 3D representation, a new visual indicator 120 corresponding to the location coordinate points derived during the eleventh second of the procedure.

When repeating steps 90-106 during the medical procedure, processor 42 receives the location signals at a sequence of times during the procedure, and the line segments rendered by the processor 42 in 3D representation 70 present a linear trace corresponding to probe locations 112 in accordance with the sequence. As described supra, the linear trace may comprise line segments 124 or continuous line 140.

While the steps presented hereinabove describe capturing location data and presenting 3D representation 70 in real-time during a medical procedure, using graph data 68 to generate and present 3D representation 70 at a later time is considered to be within the spirit and scope of the present invention. For example, prior to completing a medical procedure, medical professional 34 can review the procedure by having control console to present 3D representation 70 in a sequence of five second "windows" (i.e., time periods). Therefore, if the medical procedure included a 30 second ablation, processor 42 can present a sequence of six 3D representations 70 that trace the locations of electrode 62 during each five second time period.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for monitoring a medical procedure, comprising:
applying energy to a probe that is in contact with tissue in a cavity within a body of a living subject so as to ablate the tissue;
while applying the energy, receiving, by a processor, signals from a location transducer in the probe, which are indicative of a location of the probe in the cavity;
processing the signals so as to derive three-dimensional (3D) location coordinate points corresponding to the location of the probe at a sequence of times during which the energy was applied;
rendering to a display a 3D representation of the body cavity, and superimposing on the 3D representation visual indicators corresponding to the 3D location coordinate points at the sequence of times together with a linear trace connecting the coordinate points in accordance with the sequence;
counting, during the sequence of times, respective numbers of instances of each of the 3D location coordinate points; and
rendering a bounding sphere having a surface that encloses the visual indicators, wherein rendering the bounding sphere comprises centering the bounding sphere at a graph location in the 3D representation corresponding to 3D location point having a highest number of the instances.

2. The method according to claim 1, wherein the cavity comprises a chamber of a heart.

3. The method according to claim 1, wherein the bounding sphere comprises a minimal bounding sphere.

4. The method according to claim 1, and comprising computing a weighted average of the 3D location coordinate points, and wherein rendering the bounding sphere comprises centering the bounding sphere at a graph location in the 3D representation corresponding to the weighted average of the 3D location coordinate points.

5. The method according to claim 1, wherein the visual indicators and visual trace comprise a continuous line that traverses graph locations on the 3D representation corresponding to the sequence of coordinate points.

6. The method according to claim 1, wherein the visual trace comprises line segments connecting each sequential pair of the visual indicators.

7. The method according to claim 1, and comprising counting, during the sequence of times, respective numbers of instances of each of the 3D location coordinate points, and wherein superimposing each given visual indicator comprises rendering a given visual indicator using a color based on the respective number of instances of the given visual indicator.

8. The method according to claim 1, and comprising specifying a threshold number, and wherein upon detecting that a number of the 3D location coordinate points exceeds the threshold number, superimposing the visual indicators comprises rendering, to the display, the visual indicators corresponding to the threshold number of most recent 3D coordinate points.

9. The method according to claim 1, and comprising specifying a threshold time period, and wherein upon the sequence of times exceeding the threshold time period, superimposing the visual indicators comprises rendering, to the display, the visual indicators corresponding to the 3D coordinate points during the most recent threshold time period.

10. A method for monitoring a medical procedure, comprising:
receiving, by a processor, signals from a location transducer in a probe that is in contact with tissue in a cavity within a body of a living subject, the signals indicative of a location of the probe in the cavity;
processing the signals so as to derive three-dimensional (3D) location coordinate points corresponding to the location of the probe at a sequence of times; and
while the probe is in contact with the tissue:
rendering to a display a 3D representation of the body cavity;
superimposing on the 3D representation visual indicators corresponding to the 3D location coordinate points at the sequence of times together with a linear trace connecting the coordinate points in accordance with the sequence;
counting, during the sequence of times, respective numbers of instances of each of the 3D location coordinate points, and
rendering to the display a bounding sphere having a surface that encloses the plurality of visual indicators, wherein rendering the bounding sphere comprises centering the bounding sphere at a graph location in the 3D representation corresponding to a 3D location point having a highest number of instances.

11. The method according to claim 10, wherein the bounding sphere comprises a minimal bounding sphere.

12. The method according to claim 10, and comprising computing a weighted average of the 3D location coordinate points, and wherein rendering the bounding sphere comprises centering the bounding sphere at a graph location in the 3D representation corresponding to the weighted average of the 3D location coordinate points.

13. A medical apparatus for monitoring a medical procedure, comprising:
a probe;
a display; and
a processor configured:
to receive signals from a location transducer in a probe that is in contact with tissue in a cavity within a body of a living subject, the signals indicative of a location of the probe in the cavity;
to process the signals so as to derive three-dimensional (3D) location coordinate points corresponding to the location of the probe at a sequence of times and to count, during the sequence of times, respective numbers of instances of each of the 3D location coordinate points, and
while the probe is in contact with the tissue:
to render to the display a 3D representation of the body cavity,
to superimpose on the 3D representation visual indicators corresponding to the 3D location coordinate points at the sequence of times together with a linear trace connecting the coordinate points in accordance with the sequence, and
to render to the display a bounding sphere having a surface that encloses the plurality of visual indicators, wherein the bounding sphere is rendered by centering the bounding sphere at a graph location in the 3D representation corresponding to a 3D location point having a highest number of instances.

14. The medical apparatus according to claim 13, wherein the bounding sphere comprises a minimal bounding sphere.

15. The medical apparatus according to claim 13, wherein the processor is further configured to compute a weighted average of the 3D location coordinate points, and wherein the processor is configured to render the bounding sphere by centering the bounding sphere at a graph location in the 3D representation corresponding to the weighted average of the 3D location coordinate points.

* * * * *